US00PP24629P2

(12) United States Plant Patent
Blom

(10) Patent No.: US PP24,629 P2
(45) Date of Patent: Jul. 8, 2014

(54) *ECHINACEA* PLANT NAMED 'JULIA'

(50) Latin Name: *Echinacea hybrid*
Varietal Denomination: Julia

(76) Inventor: Arie Blom, Oudewater (NL)

( * ) Notice: Subject to any disclaimer, the term of this patent is extended or adjusted under 35 U.S.C. 154(b) by 182 days.

(21) Appl. No.: 13/507,851

(22) Filed: Aug. 1, 2012

(51) Int. Cl.
*A01H 5/00* (2006.01)

(52) U.S. Cl.
USPC ..... Plt./428

(58) Field of Classification Search
CPC ..... A01H 5/025
USPC ..... Plt./428
See application file for complete search history.

*Primary Examiner* — June Hwu
(74) *Attorney, Agent, or Firm* — Penny J. Aguirre

(57) ABSTRACT

A new cultivar of hybrid *Echinacea*, 'Julia', characterized by its large composite flowers with ray florets that are strong orange in color, its ray florets that are long and held horizontal, its strong stems, its short plant height, and its compact plant habit.

2 Drawing Sheets

Botanical classification: *Echinacea* hybrid.
Variety denomination: 'Julia'.

CROSS REFERENCE TO A RELATED APPLICATION

This application is co-pending with a U.S. Plant Patent Application filed for a plant derived from the same breeding program that is entitled *Echinacea* Plant Named 'Cleopatra' (U.S. Plant patent application Ser. No. 13/507,852).

BACKGROUND OF THE INVENTION

The present invention relates to a new and distinct cultivar of *Echinacea* of hybrid origin and will be referred to hereafter by its cultivar name, 'Julia'. 'Julia' represents a new coneflower, an herbaceous perennial grown for landscape use.

The new cultivar arose from an ongoing breeding program of the Inventor's in Zuidwolde, The Netherlands. The objective of the breeding program is to develop new cultivars of classic cone-type (non-anemone type) *Echinacea* having horizontal ray florets with unique and strong colors. The new cultivar arose from open pollination of an unnamed plant from the Inventor's breeding, designated as Ec 7001-03, in summer of 2008. The male parent is unknown. 'Julia' was selected as single unique plant from the resulting seedlings in July of 2010.

Asexual reproduction of the new cultivar was first accomplished by in vitro propagation in Heerhugowaard, The Netherlands in 2008 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Julia' as a unique cultivar of *Echinacea*.

1. 'Julia' exhibits large composite flowers with ray florets that are strong orange in color.

2. 'Julia' exhibits ray florets that are long and held horizontal.
3. 'Julia' is short in height and exhibits a compact plant habit.
4. 'Julia' exhibits strong stems.

The female parent, designated as Ec 7001-03, differs from 'Julia' in having a taller plant height and ray florets that are shorter and yellow in color. The new cultivar can be most closely compared to the cultivars 'Sunset' (U.S. Plant Pat. No. 16,424) and 'Cleopatra' (U.S. Plant patent application Ser. No. 13/507,852). 'Sunset' differs from 'Julia' in having ray florets that are lighter and more red in color, in having taller and weaker stems, and in having smaller inflorescences. 'Cleopatra' differs from 'Julia' in having smaller inflorescences and ray florets that are yellow in color.

BRIEF DESCRIPTION OF THE DRAWING

The plants in the accompanying photographs depict the characteristics of a one year-old plant of 'Julia' as field grown in Zuidwolde, The Netherlands. Stems were cut at ground level and placed in a vase for the photographs.

The photograph in FIG. 1 shows a group of cut stems.

Figure 1:
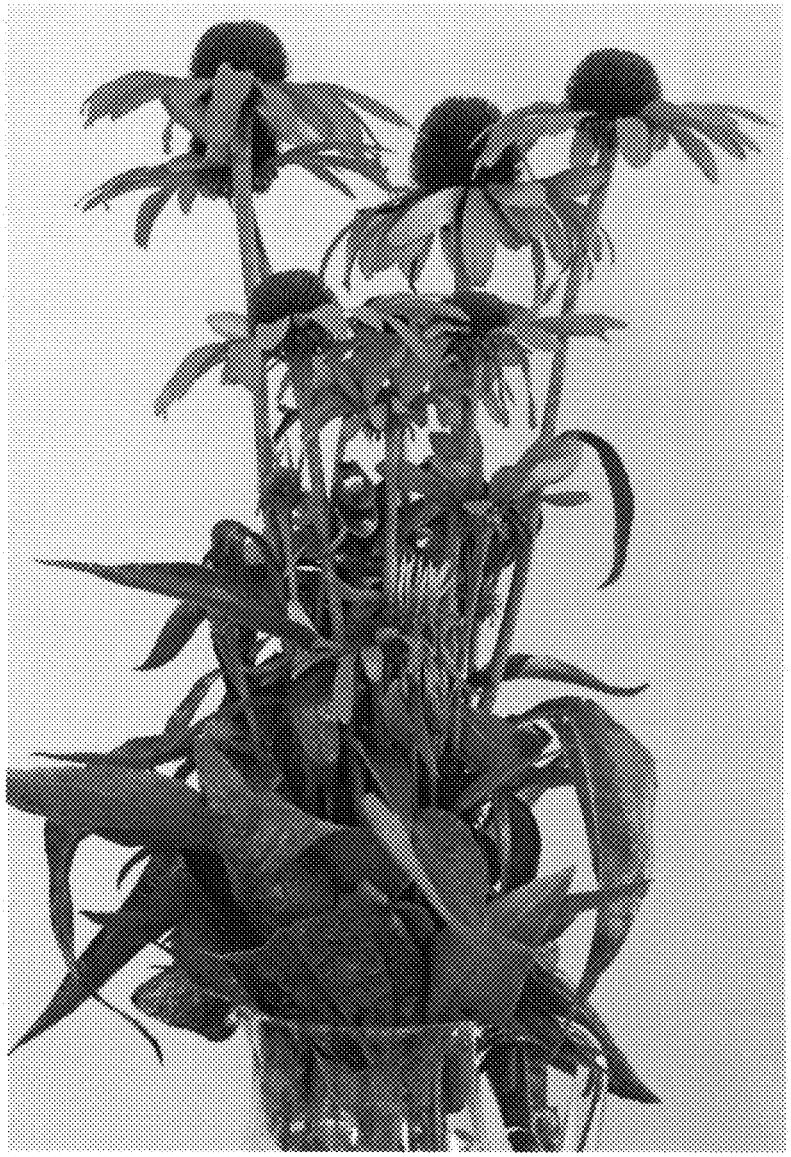
Figure 2:
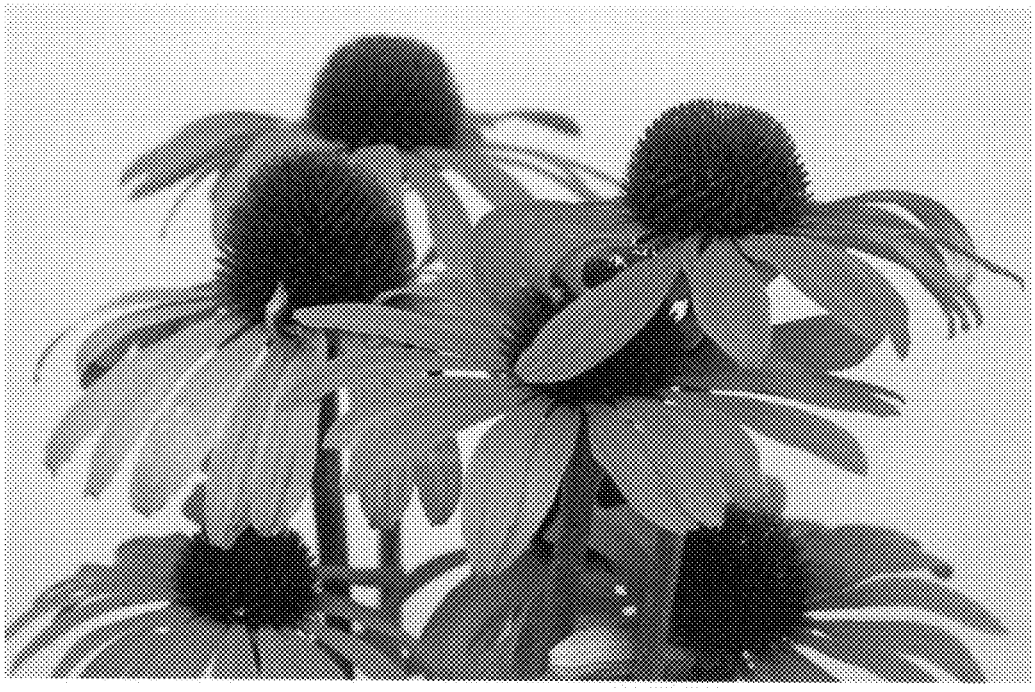

The photograph in FIG. 2 provides a close-up view of inflorescences of 'Julia'.

Figure 3:
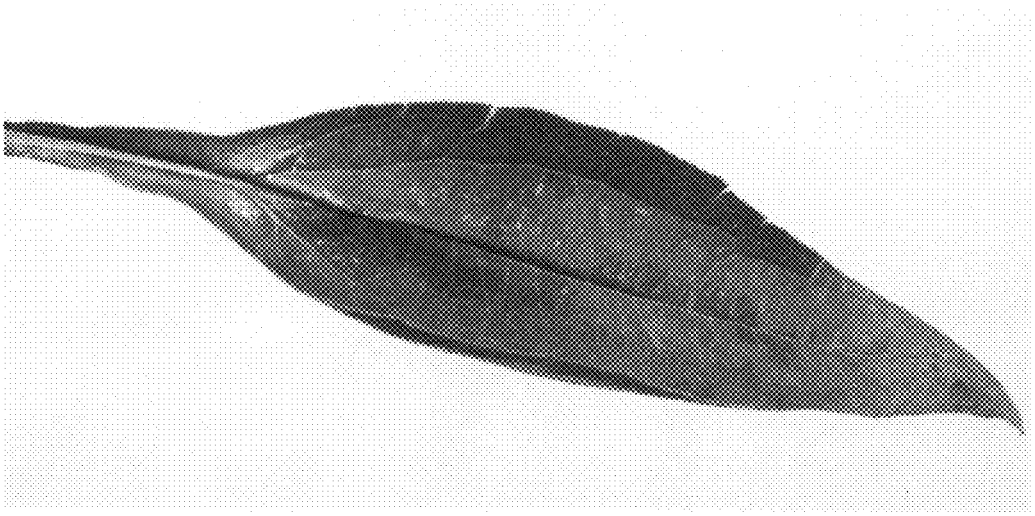

The photograph in FIG. 3 provides a close-up view of a leaf of 'Julia'.

The colors in the photograph may differ slightly from the color values cited in the detailed botanical description, which accurately describe the colors of the new *Echinacea*.

BOTANICAL DESCRIPTION OF THE PLANT

The following is a detailed description of one year-old plants of the new cultivar as field grown in Zuidwolde, The Netherlands. Plants were grown under average day temperatures ranging from 12° to 28° C. and average night temperatures of 6° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from mid June through August in The Netherlands.

*Plant habit.*—Herbaceous perennial, clump forming, upright and strong stems, compact.

*Height and spread.*—About 54.3 cm in height and 37.8 cm in spread.

*Cold hardiness.*—At least to U.S.D.A. Zones 3.

*Diseases and pests.*—No particular resistance or susceptibility to pests or diseases has been observed.

*Root description.*—Fibrous.

Growth and propagation:

*Propagation.*—Tissue culture preferred.

*Growth rate.*—Moderately vigorous.

Stem description:

*Shape.*—Rounded.

*Stem color.*—144C.

*Stem size.*—Average of 7 mm in diameter and an average of 33.9 cm in height.

*Stem surface.*—Covered with a only a few short strigose hairs; 1 mm in length, 155C in color.

*Stem strength.*—Strong.

*Stem number.*—Average of 5 on a one year-old plant.

*Branching.*—Un-branched.

Foliage description:

*Leaf shape.*—Ovate to narrowly ovate.

*Leaf division.*—Simple.

*Leaf base.*—Attenuate.

*Leaf apex.*—Acute.

*Leaf venation.*—Pinnate, upper and lower surface color; 147C.

*Leaf margins.*—Coarsely and shallowly dentate.

*Leaf attachment.*—Petiolate.

*Leaf arrangement.*—Alternate.

*Internode length.*—An average of 4.7 cm.

*Leaf size.*—Average of 13.9 cm in length and 4.7 cm in width.

*Leaf color.*—Young upper surface; 137A, young lower surface; 137C, mature upper surface; N137A, mature lower surface; 147B.

*Leaf surface.*—Upper surface is moderately glossy, lower surface is slightly glossy, both surfaces moderately covered with very short strigose hairs; average length of 0.3 mm and 156D in color.

*Petioles.*—Upper stem leaves nearly sessile, average length of petioled leaves is 6 cm in length, v-shaped petiole is about 2 mm in length and 1.5 mm in width, upper and lower surfaces smooth, color of upper and lower surfaces; 144C.

Flower description:

*Type.*—Terminal capitulum, heterogamous with ray florets around the head margin and disc florets in the center, forming a radiant head.

*Capitulum number.*—One terminal capitulum per stem.

*Lastingness of inflorescence.*—About 10 days.

*Capitulum size.*—Matures to about 2.5 cm in height and 12.4 cm in diameter, disk size is an average of 4 cm in diameter.

*Fragrance.*—Moderately faint, sweet fragrance.

*Involucral bracts or phyllary.*—About 80 arranged in 4 overlapping rows, up to 8 mm in length and 3 mm in width, dull in appearance, cuneate at base, acute apex, narrow ovate in shape, entire margins moderately covered with very short hairs; 0.4 mm in length and 157D in color, upper surface; smooth and N137B in color and sparsely covered with very short hairs average of 0.2 mm in length and 157D in color, lower surface smooth and 137A in color.

*Buds.*—Flattened globular in shape, up to 2.4 cm in diameter and 2.9 cm in length, 146A, immature ray florets 173B, tipped 151C to 151D.

*Peduncle.*—Strong, straight on top of main (flowering) stem, average angle of secondary and tertiary peduncles 20° (0°=straight upright), terminal peduncle length is 13.2, fourth peduncle length is 10 cm, diameter is peduncle is 5 mm, 145A, tinged 146B in color, surface is covered with short strigose hairs, 1 mm in length and 155C in color.

*Ray florets.*—Rotate, about 22, oblanceolate in shape, about 6.5 cm in length and 1.3 cm in width, praemorse apex, cuneate base, entire margin, held at an average angle of 5° upward near horizontal, upper surface texture is smooth and velvety and moderately ribbed lengthways (carinate), lower surface texture is slightly glossy and smooth and moderately ribbed lengthways (carinate), color: when opening upper surface; 169A to 169B, base N34A, when opening lower surface; 181D, 150B to 150C, when fully opened upper surface; between 28A and 169B to 169C, base 172A, when fully opened lower surface; 174B to 174C, tip and central band tinged 151D.

*Disc florets* (*bisexual*).—Numerous, about 350, tubular in shape, fused into tube upper 15% free, arranged spirally on disc, about 1.2 cm in length and 3 mm in width, entire margin, upper and lower surfaces smooth and glossy in appearance, color of upper and lower surfaces when opening; 145A, tip 146A, color of upper and lower surfaces when fully open; 146C, mid-section 145B.

*Receptacle.*—Narrow triangular in shape, about 1.3 cm in diameter and 1.8 cm in height, color 155D.

*Receptacle spines.*—Average of 300, acicular in shape, acute apex, attenuate base, smooth and glossy surface, color: apex; between N34A and 46A, mid-section; 145A to 145B, base; between 145D and 157D.

Reproductive organs:

*Gynoecium.*—Pistil; 1, 8 mm in length, style; 6 mm in length and 145D in color, ovary; 150D in color.

*Androcoecium.*—Stamens; 4, filament 5 mm in length and 157D in color, anther; linear in shape, 3 mm in length and 200A to 200B in color, pollen; low to moderate in quanity and 17A to 17B in color.

*Fruit/seed.*—No fruit or seed detected to date.

It is claimed:

1. A new and distinct cultivar of *Echinacea* plant named 'Julia' substantially as herein illustrated and described.

* * * * *